United States Patent [19]

Iannella

[11] Patent Number: 4,680,405
[45] Date of Patent: Jul. 14, 1987

[54] PROCESS FOR PREPARING 2-[(N-2-PYRIDYLCARBOMYL)METHYL]-SACCHARIN

[76] Inventor: Vincenzo Iannella, Viale Bianca Maria 20, Milan, Italy

[21] Appl. No.: 828,037

[22] Filed: Feb. 10, 1986

Related U.S. Application Data

[62] Division of Ser. No. 631,616, Jul. 17, 1984, Pat. No. 4,587,335, which is a division of Ser. No. 385,175, Jun. 4, 1982, Pat. No. 4,474,955.

[30] Foreign Application Priority Data

Jul. 17, 1981 [IT] Italy ................................ 22364 A/81
Aug. 7, 1981 [IT] Italy ................................ 23432 A/81

[51] Int. Cl.$^4$ ......................................... C07D 417/12
[52] U.S. Cl. ................................................ 546/270
[58] Field of Search ..................................... 546/270

[56] References Cited

U.S. PATENT DOCUMENTS 4,074,048 2/1978 Zinnes et al. ............... 546/270
4,474,955 10/1984 Iannella ...................... 544/49

OTHER PUBLICATIONS

Baylina, Chemical Abstracts, vol. 97, entry 55826g (1982).
Izquierdo Sanjose, Chemical Abstracts, vol. 97, entry 72378e (1982).
Iannella, Chemical Abstracts, vol. 98, entry 126135q (1983).
Perillo et al., Chemical Abstracts, vol. 99, entry 5574u (1983).
Chiesi Pharmaceutical, Chemical Abstracts, vol. 103, entry 123493r (1985).

Primary Examiner—John M. Ford
Attorney, Agent, or Firm—Ladas & Parry

[57] ABSTRACT

Process for preparing 2-[(N-2-pyridylcarbomoyl)methyl]saccharin of the formula

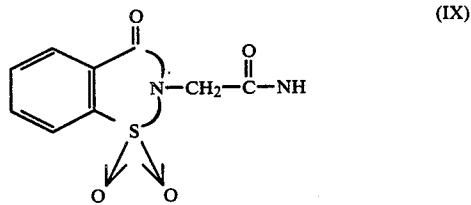

using 1-methyl-2-chloropyridine-iodine as the condensing agent. The process involves reacting a mixture of 2-aminopyridine, tri-n-butylamine and 2-carboxymethyl saccharin (VIII), in dichloromethane, in the presence of 1-methyl-2-chloropyridine iodine (X).

7 Claims, No Drawings

PROCESS FOR PREPARING 2-[(N-2-PYRIDYLCARBOMYL)METHYL]SACCHARIN

This is a divisional of Ser. No. 631,616, filed July 17, 1984, now U.S. Pat. No. 4,587,335 granted on May 6, 1986, which is a divisional of Ser. No. 385,175, filed June 4, 1982, now U.S. Pat. No. 4,474,955 granted on Oct. 2, 1984.

The present invention refers to a new process for preparing 4-hydroxy-2-methyl-2H-1,2-benzothiazine-3-[N-(2-pyridinyl)carboxamide]-1,1-dioxide and its phosphoric ester, having respectively the following structural formula:

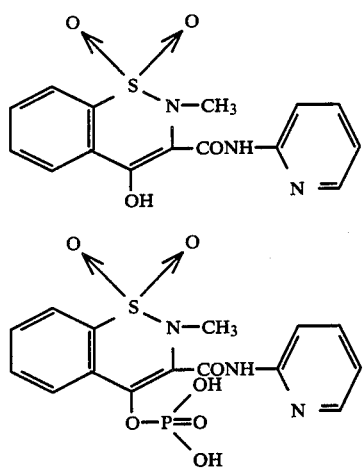

the compound (I), known under the generic name of "Piroxicam" is advantageously used therapeutically for its anti-inflammatory activity.

The compound (II) according to the invention—that is the phosphoric ester of compound (I)—is easily water-soluble, and can therefore be advantageously injected.

According to the German patent application (publ. No 1 943 265) the product of formula (I) is obtained by reacting methyl 3,4-dihydro-2-methyl-4-oxo-2H-1,2-benzothiazine-1,1-dioxide-3-carboxilate (III) with 2-aminopyridine (IV) by refluxing the xylenic solution. The starting product (III) is in turn obtained through stages will known in literature.

Methyl 3-oxo-1,2-benzothiazine-1,1-dioxide-2-acetate (V) in dimethyl sulfoxide with sodium methilate, by isomerization, gives 3,4-dihydro-4-oxo-2H-1,2-benzothiazine-1,1-dioxide-3-methyl carboxylate (VI), which is methylated with methyl iodide and sodium hydrate in methanol so that it produces the compound (III).

According to the above mentioned patent application, the synthesis is illustrated by the following scheme:

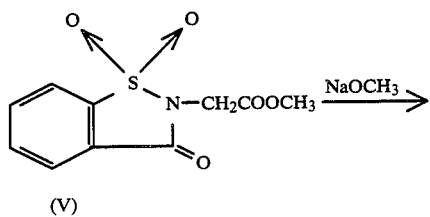

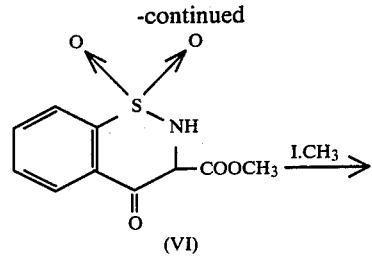

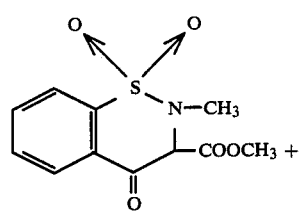

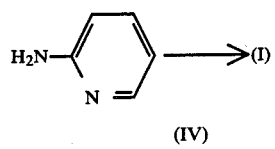

According to the U.S. Pat. No. 4,074,048, the compound (I) is obtained by reacting 4-hydroxy-N-(2-pyridyl)-2H-1,2-benzothiazine-3-carboxamide-1,1-dioxide (VII) in dimethylformamide, in the presence of sodium hydride, with methyl iodide. The starting compound (VII) is obtained through the following synthesis: 2-carboxymethyl saccharin (VIII) is reacted in tetrahydrofuran in the presence of dicyclohexyl-carbodiimide or N-ethoxycarbonyl-2-ethoxy-1,2-dihydroquinoline with 2-aminopyridine (IV) to obtain 2-[(N-2-pyridylcarbamoyl)-methyl]saccharin (IX) which is in turn isomerized to obtain the compound (VII) in the presence of sodium methylate in dimethylformamide or in dimethyl sulfoxide.

According to said U.S. patent, the synthesis is illustrated by the following scheme:

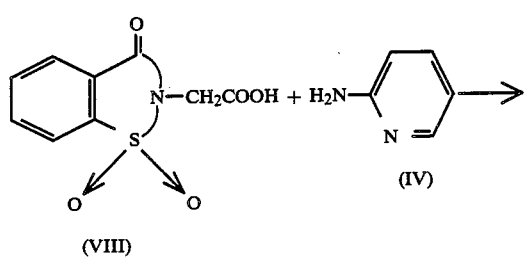

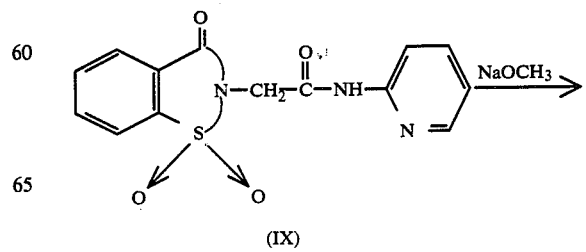

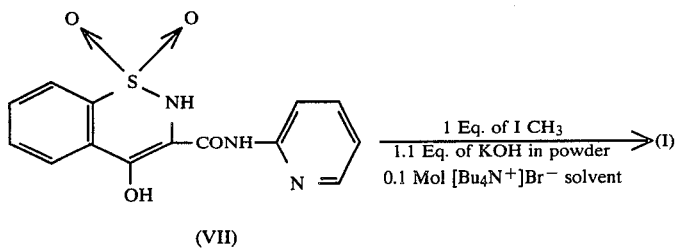

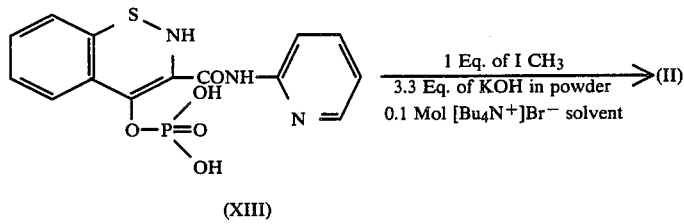

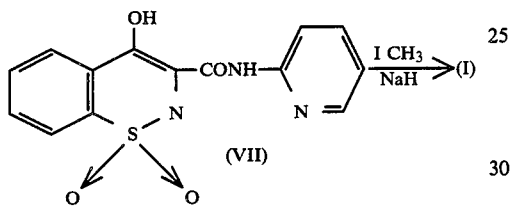

According to the teachings of the German patent application No. 1 943 265 the methylation of the intermediate (VI) gives a yield of about 55%, and the subsequent stage for the obtainment of (I) gives a yield of about 78%.

The total yield of the formation of the 'Piroxicam' product, according to this route, is therefore of about 43% altogether. According to the U.S. Pat. No. 4,074,048, the formation of the intermediate (VIII) gives a yield of about 68%, and the methylation of the compound (VII) to obtain the product named 'piroxicam' gives a yield of about 45%, the total yield being therefore of about 31%.

The main drawbacks of these methods, according to the prior art, consist in the very low yields, which become even lower if a quality product is sought as, by means of the above mentioned methods, a rather impure product is achieved.

Many advantages are provided by the process according to the invention, allowing to obtain 4-hydroxy-2-methyl-2H-1,2-benzothiazine-[N-(2-pyridyl)carboxamide]-1,1-dioxide (I) by applying the so-called 'Phase-transfer Catalysis' to effect the N-methylation. Said process follows the teachings of E. V. Dehmlow, Angew. Chem. 86,187 (1974), Angew.Chem. Int.Ed.Engl. 13,170 (1974), and consists in reacting 4-hydroxy-2H-1,2-benzothiazine-3-[N-(2-pyridyl)carboxamide]-1,1-dioxide (VII) and its ester (XIII) with methyl iodide in the presence of tetrabutyl ammonium bromide, as a catalyst, and of potassium hydroxide in powder.

As a solvent, one may equally employ acetone, dimethylformamide, dimethyl sulfoxide, dimethylethane, acetonitrile and tetrahydrofuran; the two last solvents are those preferably used.

The invention relates also to the process for obtaining the phosphoric ester of the compound (I). In particular, the syntheses according to the invention are carried out as per the following schemes:

The 'Phase-transfer Catalysis' is more advantageously employed than the known N-alkylation methods, in that it gives higher yields in very reduced times and at room temperature. In this specific case, due to the low basicity of the heterocyclic nitrogen, the use of this method is indispensable if high yield (around 90%) and a first-rate product (minimum titre 99%) are sought. Furthermore, new and more advantageous methods to produce the intermediates (VI) and (XIII) have been tested according to the invention, and namely: 2-carboxymethyl saccharin (VIII) is reacted in dichloromethane with 2-aminopyridine (VI) in the presence of 1-methyl-2-chloropyridine iodine (X) and of tri-n-butylamine (XI); there is obtained 2-[(N-2-pyridylcarbomoyl)methyl]saccharin (IX) which is isomerized by the usual techniques into 4-hydroxy-2H-1,2-benzothiazine-3-[N-(2-pyridyl)carboxamide]-1,1-dioxide (III). The phosphoric ester of this derivative is obtained by reacting the compound (VII) with phosphorous oxychloride in the presence of Pyridine.

The syntheses according to the invention are carried out as per the following scheme:

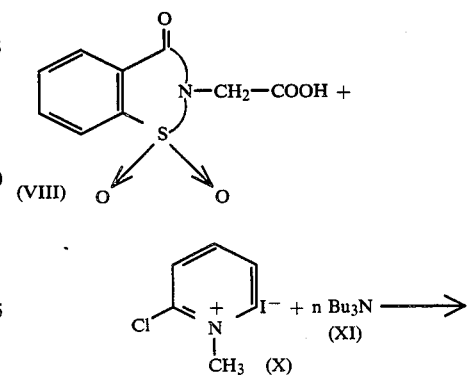

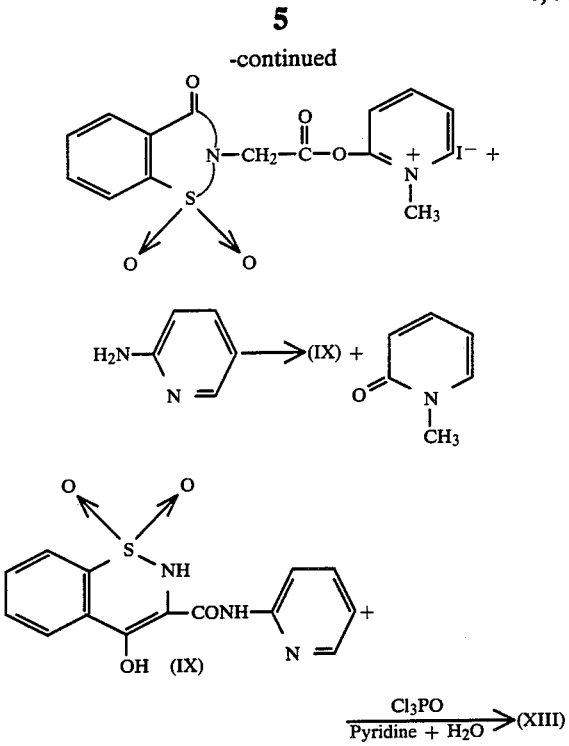

Just by way of non-limiting example, reference is being made to some ways of putting the invention into practice:

EXAMPLE 1

4-hydroxy-2-methyl-2H-1,2-benzothiazine-3-[N-(2-pyridyl)carboxamide]-1,1-dioxide (I)

A mix of 3.17 g (0.01 mols) of 4-hydroxy-N-(2-pyridyl)-2H-1,2-benzothiazine-3-carboxamide-1,1-dioxide (VII), 1.42 g (0.01 mols) of methyl iodine, 0.325 g (0.001 mols) of tetrabutyl ammonium bromide, 0.62 g (0.011 mols) of potassium hydrate in powder and 80 ml of tetrahydrofuran are energetically mixed at room temperature for one hour. The solvent is vacuum removed and the residue diluted with water. The pH is brought to 7.0 by means of HCl. The insoluble product is then filtered and crystallized from methanol and 2.98 g of (I) (yield 98%, m.p. 195°–198° C.) are obtained.

EXAMPLE 2

4-phosphonooxy-2-methyl-2H-1,2-benzothiazine-3-[N-(2-pyridyl)carboxamide]-1,1-dioxide (II)

A mix of 3.98 g (0.01 mols) of 5-phosphonooxy-N-(2-pyridyl)-2H-1,2-benzothiazine-3-carboxamide-1,1-dioxide (XIII), 1.42 g (0.01 mols) of methyl iodine, 0.325 g (0.001 mols) of tetrabutyl ammonium bromide, 1.86 g (0.033 mols) of potassium hydrate in powder and 40 ml of acetonitrile are energetically mixed at ambient temperature for one hour. The insoluble product is filtered, ethanol is added and the whole is neutralized. The sodium salt is filtered and acetone is added.

3.73 g of (II) (yield 90%; m.p. 245° C. with decomposition) precipitate.

EXAMPLE 3

2-[(N-2-pyridylcarbomoyl)methyl]saccharin (IX)

To 2.89 g (0.012 mols) of 1-methyl-2-chloropyridine iodine (X) there is added a mix of 0.94 g (0.01 mols) of 2-aminopyridine (IV), 2.4 g (0.01 mols) of 2-carboxymethyl saccharin (VIII) and 4.45 g (0.024 mols) of tri-n-butylamine in 100 ml dichloromethane. The mix is refluxed for one hour under nitrogen stream, 200 ml ether are added and the resulting mixture is washed three times with a 5% aqueous solution of hydrochloric acid. The organic layer is vacuum evaporated. The residue is crystallized from methanol.

2.68 g of (IX) (yield 85%; m.p. 176°–178° C.) are obtained.

EXAMPLE 4

4-hydroxy-N-(2-pyridyl)-2H-1,2-benzothiazine-3-carboxamide-1,1-dioxide (VII)

To a solution of 1.6 g (0.005 mols) of (IX) warm dissolved in 5 ml dimethyl sulfoxide there are added 0.80 g (0.015 mols) of sodium methylate.

The whole is heated under stirring for 15' at 80°–90° C. The mixture is poured in iced water and acidificated with acetic acid, and the yellow precipitate (about 0.7 g of (VII) with m.p. 222°–224° C.) is filtered.

EXAMPLE 5

4-phosphonooxy-N-(2-pyridyl)-2H-1,2-benzothiazine-3-carboxamide-1,1-dioxide (XIII)

1.68 g (0.011 mols) of phosphorous oxychloride are dissolved in 10 ml pyridine at 20° C.

To the solution kept at 20° C. there are added under stirring in 5 minutes' time 20 ml pyridine wherein 3.17 g (0.01 mols) of (VII) have been previously dissolved. The solution is kept at 20° C. for 10', then the temperature is slowly allowed to rise, in 10', to 0° C. There are added under stirring 10 ml iced water and then a 10% solution of sodium hydrate until the pH is 8.0.

The solution is extracted by means of chloroform.

The aqueous solution which separates is acidificated, treated with vegetal charcoal, filtered and vacuum dried. The residue is dissolved in absolute alcohol. The compound (XIII) is filtered and precipitated with addition of acetone.

4.3. g of product (m.p. 260°–261° C.) are obtained.

With regard to the phosphoric ester, clinical and pharmacological tests have been carried out, through which the following results have been achieved:

the active ingredient of Piroxafos, namely the piroxicam phosphate, has low acute toxicity when administered by the oral, subcutaneous and parenteral route to the mouse and rat; if administered subcutaneously to the rat over a period of time much longer than that usually provided for according to clinical practice (45 days), Piroxafos is found to be well tolerated in doses corresponding to 8.3 DTD maximum (2.5 mg/Kg); in doses corresponding to 16.6 DTD max. (5 mg/Kg) the prolonged treatment causes a 25% death rate as well as a toxic symptomatology (such as decrease in weight, anaemia, increase in azotemia and in SGPT and lesions of gastroenteric mucosa);

if administered subcutaneously to the dog in doses of 2 DTD max. over 45 days consecutively, the drug is well tolerated and causes no toxic effects;

if administered by the rectal route to the rabbit under the form of suppositories for 30 consecutively in doses corresponding to 10 DTD max., the Piroxafos is well tolerated and without any general and topical toxic effects;

if administered to the rat for 180 days consecutively, in oral doses 5 and 10 times higher than the DTD max. (4 and 8 mg/Kg), the Piroxafos does not badly affect the biological and hematochemical parameters, though it may have irritating effects on the gastroenteric mucosa, and this only if administered in the highest doses;

oral doses corresponding to 5 DTD max. administered to the dog over 180 days consecutively are well tolerated and cause no toxic effects;

if administered to the rat 8 days before fecundation and until the 18th day of gestation in doses corresponding to 5 and 10 DTD max., the Piroxafos has no negative effect on the reproduction function, the advancement of pregnancy and the embryofetal and neonatal development;

if administered to the rabbit from the 5th to the 17th day of gestation, in doses of 5 and 10 DTD max. by the oral route, and of 10 DTD max. by the rectal route, the Piroxafos has no teratogenic effects;

the Piroxafos does not cause any alterations in the arterial pressure, breath and ECG basic values, after oral, subcutaneous and intraperitoneal treatment in doses 10 and 30 times higher than the average DTS adopted in the clinical field.

the ulcerogenic activity of Piroxafos, when administered in doses of 20 mg/Kg corresponding to 50 average DTS, is decidedly lower than that exerted by indomethacin ((10 mg/Kg);

after being tested on the rat and mouse according to different experimental methods, the Piroxafos proved to exert, in doses of 4 and 8 mg/Kg, an antiinflammatory, analgetic and antipyretic activity.

I claim:

1. A process for preparing 2-[(N-2-pyridylcarbomoyl)-methyl]saccharin (IX) comprising reacting a mixture of 2-carboxymethyl saccharin (VIII), 2-aminopyridine (IV) and tri-n-butylamine, in dichloromethane, with 1-methyl-2-chloropyridine iodine (X); and recovering the resulting 2-[(N-2-pyridylcarbomoyl)methyl]saccharin (IX).

2. A process as in claim 1 wherein 0.01 moles of 2-carboxymethyl saccharin (VIII), 0.01 moles of 2-aminopyridine and 0.024 moles of tri-n-butylamine (XI), in dichloromethane, are reacted with 0.01 moles of 1-methyl-2-chloropyridine iodine (X).

3. A process as in claim 2 wherein said reaction occurs in 100 mls of dichloromethane.

4. A process as in claim 3 further comprising refluxing the reaction mixture for about one hour under nitrogen steam.

5. A process as in claim 4 wherein the recovery of 2-[(N-2-pyridylcarbomoyl)methyl]saccharin (IX) is effected by adding ether to the reaction mixture, washing the resulting mixture three times with a 5% aqueous solution of hydrochloric acid, vacuum evaporating the organic layer, and crystallizing the residue from methanol.

6. A process for preparing 2-[N-2-pyridylcarbomoyl)-methyl]saccharin (IX) comprising reacting a mixture of 2-carboxymethyl saccharin (VIII), 2-aminopyridine (IV) and tri-n-butylamine in an organic solvent with 1-methyl-2-chloropyridine iodine (X) and recovering the resulting 2-[(N-2-pyridylcarbomoyl)methyl]saccharin (IX).

7. A process as in claim 6 wherein 0.01 moles of 2-carboxymethyl saccharin (VIII), 0.01 moles of 2-aminopyridine and 0.024 moles of tri-n-butylamine (XI) are reacted with 0.01 moles of 1-methyl-2-chloropyridine iodine (X).

* * * * *

UNITED STATES PATENT AND TRADEMARK OFFICE
CERTIFICATE OF CORRECTION

PATENT NO. : 4,680,405

DATED : July 14, 1987

INVENTOR(S) : Vincenzo IANNELLA

It is certified that error appears in the above-identified patent and that said Letters Patent is hereby corrected as shown below:

```
Title Page, Column 1, delete foreign
  priority application date "Jul   17, 1981"
  and replace therefor -- June 17, 1981 --
```

Signed and Sealed this

Third Day of January, 1989

Attest:

DONALD J. QUIGG

*Attesting Officer*   *Commissioner of Patents and Trademarks*